United States Patent [19]

Nobuhiro et al.

[11] Patent Number: 6,057,372
[45] Date of Patent: May 2, 2000

[54] ANTIBACTERIAL AGENTS AND COSMETICS AND CLOTHING CONTAINING THE SAME

[75] Inventors: Akio Nobuhiro; Yutaka Kato; Akio Hasebe, all of Noda, Japan

[73] Assignee: Soda Aromatic Co., Ltd., Japan

[21] Appl. No.: 09/011,335

[22] PCT Filed: May 21, 1997

[86] PCT No.: PCT/JP97/01710

§ 371 Date: Feb. 10, 1998

§ 102(e) Date: Feb. 10, 1998

[87] PCT Pub. No.: WO97/47294

PCT Pub. Date: Dec. 18, 1997

[30] Foreign Application Priority Data

Jun. 11, 1996 [JP] Japan ................................. 8-172991
Sep. 11, 1996 [JP] Japan ................................. 8-263719

[51] Int. Cl.$^7$ .................................................. A61K 31/12
[52] U.S. Cl. ........................... 514/675; 680/685; 680/859
[58] Field of Search ................................ 514/675, 680, 514/685, 859

[56] References Cited

U.S. PATENT DOCUMENTS

| 3,503,994 | 3/1970 | Hodge et al. | 260/343.2 |
| 5,023,252 | 6/1991 | Hseih | 514/183 |
| 5,342,852 | 8/1994 | Hedge et al. | 514/461 |
| 5,378,626 | 1/1995 | Horan | 435/252.1 |
| 5,731,303 | 3/1998 | Hsieh | 514/183 |

*Primary Examiner*—Kevin E. Weddington
*Attorney, Agent, or Firm*—Austin R. Miller

[57] ABSTRACT

Safe antibacterial agents containing macrocyclic lactones and/or macrocyclic ketones usable for suppressing the growth of indigenous dermal bacteria. Cosmetics containing these antibacterial agents can, in particular, suppress the evolution of the body odor and are efficacious in preventing and treating pimples. When introduced into clothing, these antibacterial agents achieve an antibacterial/deodorizing effect.

12 Claims, No Drawings

ANTIBACTERIAL AGENTS AND COSMETICS AND CLOTHING CONTAINING THE SAME

This application is a 371 of PCT/JP97/01710 filed May 21, 1997.

TECHNICAL FIELD OF THE INVENTION

The present invention relates to antibacterial agents used for suppressing the growth of indigenous dermal bacteria present in derma of the human body, etc., and specifically safe antibacterial agents efficacious in suppressing the evolution of the body odor and in preventing pimples, and fragrant cosmetics and clothing containing or impregnating carrying such antibacterial agents.

BACKGROUND ART OF THE INVENTION

Body odor of the human body, etc. is evolved by indigenous dermal bacteria that decompose secreta from sweat glands or sebaceous glands. Generally, as indigenous dermal bacteria, bacteria of the genus Micrococcus and the genus Staphylococcus which are Gram-positive cocci, and bacteria of the genus Corynebacterium, the genus Propionibacterium and the genus Brevibacterium which are Gram-positive rods and coryneform bacteria (polymorphic type), are known, and it is known that bacteria causing odor of the armpit, which is particularly a problem, are coryneform bacteria. The main components of the decomposition products due to such indigenous dermal bacteria are fatty acids having a carbon number of not more than 10, such as acetic acid, propionic acid, isobutyric acid, isovaleric acid, caproic acid and capric acid.

As conventional methods for removing or deodorizing such a body odor, suppressing the body odor by a bactericide or an antisweat agent or masking the body odor by an aromatic is performed. However, with respect to the conventional bactericides, the minimum use thereof is desired from a problem of safety in the human body, and also with respect to antisweat agents, the use thereof is limited only to application to specific local areas because it suppresses important physiological function of the human body. Therefore, for example, at a portion such as the armpit, where sweat and sebum are secreted and indigenous dermal bacteria are likely to grow, it is difficult to sufficiently prevent body odor. Further, masking body odor by an aromatic is likely to cause malodor by mixing of the smell of the aromatic and the body odor.

In order to solve such problems, some antibacterial agents safe to the human body are proposed. For example, in JP-A-SHO 61-291503, an antibacterial/anticultural agent, whose active ingredient is a mixture of the sap of yucca and an acid such as acetic acid or propionic acid, is proposed. However, because acetic acid or propionic acid itself is a component evolving malodor of the body odor, such an agent is not always practical.

In JP-A-SHO 60-42765 and JP-A-HEI 2-40043, an antibacterial agent, which contains natural farnesol and a synthetic farnesol as its active ingredients, is disclosed. Although these active ingredients are efficacious against bacteria of the genus Staphylococcus, they are weak in antibacterial properties against bacteria of the genus Corynebacterium, and data of antibacterial property to other indigenous dermal bacteria such as bacteria of the genus Propionibacterium are not disclosed.

Further, in JP-A-HEI 8-40861, a method for preventing and treating the foot odor using a monoglycerine ester of a middle chain fatty acid is proposed. Even in this method, because a component evolving malodor such as caprylic acid or capric acid is generated from the monoglycerine ester of the middle chain fatty acid by lipase action caused by indigenous dermal bacteria, it is not always practical.

Pimples are a dermal disease expressed mainly in puberty and the disease is called acne, and clinically they are defined as "chronic inflammatory variation generating in pores around the hair follicle fatty gland". Although pimples are a dermal disease caused by complicatedly entangled factors, generally it is considered that excessive secretion of sebum, cornification of hair follicles and bacteria in hair follicles have an important function therefor.

It is known that bacteria causing pimples are Propionibacterium acnes which are coryneform bacteria. The bacteria grow in trichocyte, produce lipase and hydrolyze triglyceride which is a major component in sebum, thereby producing free fatty acid and causing local inflammation. This is considered to be a main reason for generation of pimples.

As conventional methods for preventing or treating such pimples, suppression of secretion of sebum by female sex hormones, sterilization by antibiotics etc. and breakaway of keratin by sulfur etc. are conducted. However, there is a fear of side effects in use of female sex hormones, in use of antibiotics there is a fear which also breaks a microbial flora on derma useful to the human body, and in use of sulfur there is a problem in stimulation of derma and generation of sulfur smell.

From such circumstances, development of safe antibacterial agents which can suppress the growth of indigenous dermal bacteria and suppress the evolution of body odor even in a portion where sweat or sebum is much secreted in the human body, and development of safe antibacterial agents which are efficacious in suppressing the body odor and preventing and treating pimples without breaking microbial flora of indigenous dermal bacteria by preferentially suppressing coryneform bacteria which cause the armpit odor or pimples, are required.

DISCLOSURE OF THE INVENTION

As the result of earnest investigation to satisfy the above-described requirements, the inventors of the present invention have found that specified macrocyclic lactones and macrocyclic ketones, which are synthetic aromatics of a musky odor, among aromatic compounds indicate strong antibacterial properties against indigenous dermal bacteria.

An object of the present invention is to provide antibacterial agents which can be applied to various uses for suppressing the growth of indigenous dermal bacteria, specifically, safe antibacterial agents efficacious in suppressing body odor and preventing pimples, particularly, useful for application in cosmetics and in clothing.

Another object of the present invention is to provide fragrant cosmetics containing the forgoing antibacterial agents, and useful in clothing for impregnating the antibacterial agents.

The, the macrocyclic lactones themselves are known aromatic compounds. Although it is described in Japanese cosmetics technology conference report (Sawano et al., 1993, Vol. 27 (3), page 227) that a form of macrocyclic lactone, for example, 15-pentadecanolide (or cyclopentadecanolide) indicates an antibacterial property against bacteria of the genus Arthrobacter, it does not disclose at all that such a macrocyclic lactone has an antibacterial action against bacteria of the genus Staphylococcus, the genus Corynebacterium, etc. which are indigenous dermal bacteria.

To accomplish the above-described objects, an antibacterial agent according to the present invention contains at least one of a macrocyclic lactone represented by the following chemical formula (1) (In the formula, "n" is an integer in the range of 0–2, the portions shown by "---" are single bonds or any one portions shown by "---" is a double bond and/or and a macrocyclic ketone represented by the following chemical formula (2), in which, "n" is an integer in the range of 0–2, R is a hydrogen atom or a methyl group, the portions shown by "---" are single bonds or any one portion of the portions shown by "---" is a double bond.

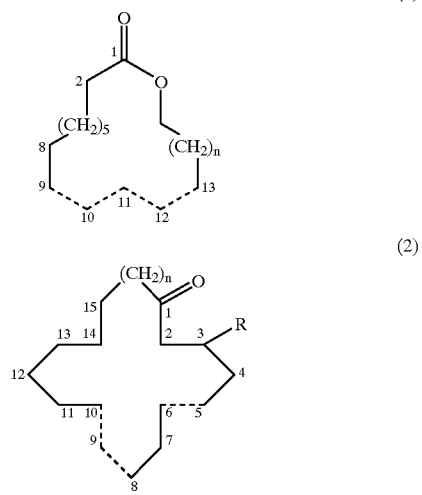

In the above described chemical formulae (1) and (2), in a case where the portions shown by "---" are single bonds, it is indicated that the macrocyclic lactone or the macrocyclic ketone is a saturated compound, and in a case where any one portions shown by "---" is a double bond, it is indicated that the macrocyclic lactone or the macrocyclic ketone is an unsaturated compound. Where, that "any one portion of the portions shown by "---" is a double bond" means that only any one portion among a plurality of portions shown by "---" is a double bond for example, in the case of the chemical formula of the above-described macrocyclic ketone, means that only and one portion among three portions indicated by 5-, 8-and 9-positions is a double bond.

The above described macrocyclic lactone comprises, for example, at least one lactone selected from the group consisting of 14-tetradecanolide, 15-pentadecanolide, 11(or 12)-pentadecen-15-olide, 16-hexadecanolide and 9-hexadecen-16-olide. Among these, particularly, 14-tetradecanolide, 15-pentadecanolide and 11(or 12)-pentadecen-15-olide are preferred. The above-described macrocyclic ketone comprises, for example, at least one ketone selected from the group consisting of cyclopentadecanone, 3-methyl-cyclopentadecanone, cyclohexadecanone, 5-cyclohexadecen-1-one, 8-cyclohexadecen-1-one, cycloheptadecanone and 9-cycloheptadecen-1-one.

Such an antibacterial agent indicates an excellent property for suppressing the growth of bacteria, specifically against coryneform bacteria which are Gram-positive rods, in particular, against bacteria of the genus Corynebacterium which affect evolution or acceleration of the armpit odor or Propionibacterium acnes which affect generation of pimples.

Therefore, this antibacterial agent has an excellent property for suppressing body odor or/and an excellent property for suppressing pimples, an excellent property for suppressing body odor or/and the excellent property for suppressing pimples can be obtained by administering it in cosmetics used for suppressing body odor pimples, and an excellent antibacterial/deodorizing effect can be obtained by impregnating it into fibers or clothing, particularly into clothing coming into contact directly with the skin such as underwear, shirts, undergarments and socks.

THE BEST MODE FOR CARRYING OUT THE INVENTION

The antibacterial agent according to the present invention contains at least one of a macrocyclic lactone represented by the aforementioned chemical formula (1) and/or a macrocyclic ketone represented by the aforementioned chemical formula (2). First, the antibacterial agent containing the macrocyclic lactone (1) will be explained.

Although it has been reported that a kind of lactone among known aromatic compounds indicates an antibacterial property against specified bacteria, the antibacterial property of a macrocyclic lactone is not reported so much.

Surprisingly, a specified macrocyclic lactone represented by the aforementioned chemical formula (1) according to the present invention indicates a strong antibacterial property against Gram-positive bacteria of the genus Micrococcus, the genus Staphylococcus, the genus Corynebacterium, the genus Propionibacterium, etc., and can suppress body odor by suppressing the growth of these bacteria. Further, because pimples, which generate mainly in fat-leaking portions on the head, the face, the breast and the backs of males and females in puberty and younger days in which secretion of fatty glands is active, are caused mainly by the growth of Propionibacterium acnes, the macrocyclic lactone according to the present invention effective for suppressing this growth is also efficacious in preventing pimples.

The macrocyclic lactone according to the present invention can be prepared according to a regular method by synthesizing ω-oxyfatty acid and by intramolecular ring closing.

The macrocyclic lactone used in the present invention is good in biodegradation and toxicity is not recognized, and therefore, it does not affect the ecosystem even if it is discharged in the environment. It is safe to the human body.

Accordingly, because the antibacterial agent according to the present invention indicates a property for suppressing growth particularly against indigenous dermal bacteria, it is preferably used by application to cosmetics and clothes objectifying the human body. As to cosmetics, hair care products such as shampoo, rinse, hair tonic and hair promoter, body cleaners such as soap and body shampoo, antisweat or deodorant products for armpit or foot, etc. can be raised, and the antibacterial agent according to the present invention can be used by addition to these cosmetics. Although the amount of addition thereof may vary depending upon the kind or the purpose for use of the cosmetics, the amount is preferably in the range of 0.001–10 wt. % relative to the total weight, more preferably in the range of 0.01–5 wt. %. Further, it is possible to obtain an antibacterial/deodorizing effect by impregnating the antibacterial agent according to the present invention into clothes such as underwear and socks. The impregnation of the antibacterial agent into clothes can be performed by a method such as coating, dipping or spraying, and preferably, it can be impregnated at the time of cleaning or washing of clothes by adding it to a detergent. In a case where the cloth is composed of synthetic fibers, the antibacterial agent may be mixed at the time of melt-spinning.

Next, the antibacterial agent containing the macrocyclic ketone represented by the chemical formula (2) will be explained.

The macrocyclic ketone represented by the aforementioned chemical formula (2) according to the present invention has a particular property for suppressing the growth of indigenous dermal coryneform bacteria, and has an effect to suppress body odor and to prevent and treat pimples without breaking the microbial flora of indigenous dermal bacteria.

The macrocyclic ketone according to the present invention can be prepared according to a regular method by ring expansion using cyclododecanone as the raw material, and it may be an optically active substance.

The macrocyclic ketone used in the present invention is also good in biodegradation and toxicity is not recognized, and therefore, it does not affect the ecosystem even if it is discharged in the environment. It is safe to the human body. Accordingly, the antibacterial agent according to the present invention containing this macrocyclic ketone is preferably applied to various cosmetics and clothes similarly to the above-described antibacterial agent containing the macrocyclic lactone. Although the amount of addition thereof may vary depending upon the kind or the purpose for use of the cosmetics, the amount is preferably in the range of 0.001–10 wt. % relative to the total weight, more preferably in the range of 0.01–5 wt. %.

Further, it is possible to obtain an antibacterial/deodorizing effect by impregnating the antibacterial agent containing this macrocyclic ketone into clothes such as underwear and socks. The impregnation of the antibacterial agent into clothes can be performed by a method such as coating, dipping or spraying, as aforementioned. Further, in a case where the cloth is composed of synthetic fibers, the antibacterial agent may be mixed at the time of melt-spinning.

It is possible that the above-described macrocyclic lactone and macrocyclic ketone are together contained in the antibacterial agent. Even in this case, the amount of addition of the antibacterial agent is preferably in the range of 0.001–10 wt. %, and more preferably in the range of 0.01–5 wt. %, relative to the total weight of the cosmetic.

In the antibacterial agents and the cosmetics and clothes using the antibacterial agents according to the present invention, as long as the advantages according to the present invention are not damaged, supplementary components, such as another antibacterial agent, astringent, bactericide, dermal secretion retarder, keratin breakaway agent, surfactant, thickener, aromatic, pigment, alcohol and water, may be together used.

According to the above-described antibacterial agents of the present invention, antibacterial agents suitable to various uses for suppressing the growth of indigenous dermal bacteria, particularly, suitable to safe cosmetics and fibers and clothes efficacious in suppressing the body odor and in preventing and treating pimples, can be obtained.

Further, the macrocyclic lactone and macrocyclic ketone according to the present invention indicate a particular, selective property for suppressing, in particular, the growth of indigenous dermal coryneform bacteria, and have an effect to suppress body odor and to prevent and treat pimples without breaking the microbial flora of indigenous dermal bacteria. Because these macrocyclic lactones and macrocyclic ketones are good in biodegradation and toxicity is not recognized, they do not affect the ecosystem even if they are discharged in the environment as waste, and they are safe to the human body.

Moreover, because the cosmetics containing the above-described antibacterial agents are fragrant, for example, if the antibacterial agents are added to cosmetics containing sulfur for preventing or treating pimples, not only the antibacterial effect but also a masking effect of sulfur smell by the musk-like fragrance can be obtained. Further, in the clothes impregnated with the antibacterial agents, body odor can be suppressed in an environment soft to the skin as well as the fragrance can be given.

Next, the present invention will be explained based on examinations and examples.

First, the antibacterial agents and the cosmetics containing the macrocyclic lactone according to the present invention will be explained.

(Examination)

Using the following liquids prepared for the test, 7 kinds of strains and 2 kinds of culture media, the examination of antibacterial property with respect to the macrocyclic lactone was performed.

Prepared Test Liquids:

The solution mixing each of the following test compounds (macrocyclic lactones) and polyoxyethylene cured castor oil (40 E.O. [additional mol number of ethylene oxide: 40]) at equal contents was used after diluting it ten times with distilled water. As a comparison, isopropylmethylphenol, which was a bactericide, was used as the test liquid.

Macrocyclic Lactones:

No. 1: 12-dodecanolide (saturated compound)

No. 2: 13-tridecanolide (saturated compound)

No. 3: 14-tetradecanolide (saturated compound)

No. 4: 15-pentadecanolide (saturated compound)

No. 5: 11(or 12)-pentadecen-15-olide (unsaturated compound)

No. 6: 16-hexadecanolide (saturated compound)

No. 7: 9-hexadecen-16-olide (unsaturated compound)

Comparison (bactericide):

No. 8: isopropylmethylphenol

Used Strains:

Gram-positive-aerobic bacteria

Micrococcus sp. (referred to as "M.sp")

*Staphylococcus epidermidis* (referred to as "*S.e*")

*Staphylococcus aureus* (referred to as "*S.a*")

Corynebacterium sp. (referred to as "C.sp")

Gram-positive-anaerobic bacteria

*Propionibacterium acnes* (referred to as "*P.a*")

Gram-negative-aerobic bacteria

*Pseudomonas aeruginosa* (referred to as "*Ps.a*")

Gram-negative-anaerobic bacteria

*Escherichia coli* (referred to as "*E.c*")

Used Culture Media:

For aerobic bacteria: normal bouillon medium (produced by Eiken Chemical Corporation)

For anaerobic bacteria: GAM bouillon "Nissui" (produced by Nissui Seiyaku Corporation)

Each culture medium of 100 ml was put in an Erlenmeyer flask having a capacity of 500 ml, a suspension of each of the bacteria was inoculated to achieve $10^6$ CFU/ml (colony forming units/ml), the test liquid was added into it so that the concentration of the test compound became 0 (blank), 10 and 100 ppm, respectively, as shown in Table 1, and after a silicone gas-permeable plug was attached, at 37° C. for 24 hours, 80 rpm reciprocally shaking culture was conducted as to the aerobe and static culture was conducted as to the anaerobe, respectively. Thereafter, the turbidity of the culture liquid (absorbance at a wave length of 660 nm) was determined.

As a result, as shown in Table 1, the macrocyclic lactones did not indicate a growth suppressing property against Gram-negative bacteria but indicated a growth suppressing property against Gram-positive bacteria, and in particular, strong growth suppressing properties could be recognized in 14-tetradecanolide having a carbon number of 14 and 15-pentradecanolide and 11(or 12)-pentadecen-15-olide having a carbon number of 15.

TABLE 1

| Macro-cyclic lactone No. | Concentration ppm | Used Strain | | | | | | |
|---|---|---|---|---|---|---|---|---|
| | | M.sp | S.e | S.a | C.sp | P.a | Ps.a | E.c |
| 1 | 0 | + | + | + | + | + | + | + |
| | 10 | + | + | + | + | + | + | + |
| | 100 | − | − | − | − | − | + | + |
| 2 | 0 | + | + | + | + | + | + | + |
| | 10 | + | + | + | + | + | + | + |
| | 100 | − | − | − | − | − | + | + |
| 3 | 0 | + | + | + | + | + | + | + |
| | 10 | − | − | − | − | − | + | + |
| | 100 | − | − | − | − | − | + | + |
| 4 | 0 | + | + | + | + | + | + | + |
| | 10 | − | + | − | − | + | + | + |
| | 100 | − | − | − | − | − | + | + |
| 5 | 0 | + | + | + | + | + | + | + |
| | 10 | − | + | − | − | − | + | + |
| | 100 | − | − | − | − | − | + | + |
| 6 | 0 | + | + | + | + | + | + | + |
| | 10 | + | + | + | − | + | + | + |
| | 100 | − | − | − | − | − | + | + |
| 7 | 0 | + | + | + | + | + | + | + |
| | 10 | + | + | + | + | + | + | + |
| | 100 | − | − | − | − | − | + | + |
| 8 (Comparison) | 0 | + | + | + | + | + | + | + |
| | 10 | + | + | + | + | + | + | + |
| | 100 | − | − | − | − | − | + | + |

−: growth; none
+: growth; present

EXAMPLES

Examples 1, 2 and Comparative Example 1 (hair tonic)

Each of 10 males used the hair tonics of Example 1 and Comparative Example 1 shown in Table 2 and the hair tonic of EXAMPLE 2 shown in Table 3 after washing of the hair by a shampoo, and the effect for suppressing the smell of the head skin after 10 hours was estimated. As a result, as shown in table 4, in the hair tonics of Examples 1 and 2, an effect for suppressing the smell of the head skin could be clearly recognized as compared with the hair tonic of Comparative Example 1.

TABLE 2

| Component | Example 1 (wt. %) | Comparative Example 1 (wt. %) |
|---|---|---|
| 14-tetradecanolide | 0.3 | — |
| ethanol | 60.0 | 60.0 |
| polyoxyethylene oleylalcohol(20 E.O.) | 1.0 | 1.0 |

TABLE 2-continued

| Component | Example 1 (wt. %) | Comparative Example 1 (wt. %) |
|---|---|---|
| aromatic | 0.2 | 0.2 |
| distilled water | remaining amount | remaining amount |

TABLE 3

| Example | Example 2 (wt. %) |
|---|---|
| 15-pentadecanolide | 0.3 |
| ethanol | 60.0 |
| polyoxyethylene oleylalcohol(20 E.O.) | 1.0 |
| aromatic | 0.2 |
| distilled water | remaining amount |

TABLE 4

| Estimation | Example 1 (Number of persons) | Example 2 (Number of persons) | Comparative Example 1 (Number of persons) |
|---|---|---|---|
| Very efficacious | 7 | 8 | 0 |
| Efficacious | 2 | 1 | 2 |
| A little efficacious | 1 | 1 | 2 |
| Not efficacious | 0 | 0 | 6 |
| Deteriorated | 0 | 0 | 0 |

Examples 3–5 and Comparative Example 2 (deodorant lotion)

Each of 10 males having the armpit odor applied the deodorant lotions of Examples 3 and 4 and Comparative Example 2 shown in Table 5 and the deodorant lotion of Example 5 shown in Table 6 on the armpit after taking a bath, and the effect for suppressing the armpit odor after 10 hours was estimated. As a result, as shown in Table 7, in the deodorant lotions of Examples 3–5, an effect for suppressing the armpit odor could be clearly recognized as compared with the deodorant lotion of Comparative Example 2.

TABLE 5

| Component | Example 3 (wt. %) | Example 4 (wt. %) | Comparative Example 2 (wt. %) |
|---|---|---|---|
| 15-pentadecanolide | 0.1 | 1.0 | — |
| chlorohydroxyl aluminium | 10.0 | 10.0 | 10.0 |
| ethanol | 70.0 | 70.0 | 70.0 |
| polyoxyethylene oleylalcohol(20 E.O.) | 1.5 | 1.5 | 1.5 |
| aromatic | 0.1 | 0.1 | 0.1 |
| distilled water | remaining amount | remaining amount | remaining amount |

TABLE 6

| Component | Example 5 (wt. %) |
| --- | --- |
| 11 (or 12)-pentadecen-15-olide | 1.0 |
| chlorohydroxyl aluminium | 10.0 |
| ethanol | 70.0 |
| polyoxyethylene oleylalcohol(20 E.O.) | 1.5 |
| aromatic | 0.1 |
| distilled water | remaining amount |

TABLE 7

| Estimation | Example 3 (Number of persons) | Example 4 (Number of persons) | Example 5 (Number of persons) | Comparative Example 2 (Number of persons) |
| --- | --- | --- | --- | --- |
| Very efficacious | 9 | 10 | 10 | 0 |
| Efficacious | 1 | 0 | 0 | 3 |
| A little efficacious | 0 | 0 | 0 | 6 |
| Not efficacious | 0 | 0 | 0 | 1 |
| Deteriorated | 0 | 0 | 0 | 0 |

Next, the antibacterial agents and the cosmetics containing the macrocyclic ketone according to the present invention will be explained.

(Examination)

Using the following 7 kinds of liquids prepared for the test, 7 kinds of strains and 2 kinds of culture media, the examination of antibacterial property was performed. Prepared test liquids:

The solution mixing each of the following No. 1–7 macrocyclic ketones and polyoxyethylene cured castor oil (40 E.O.) at equal contents was used after diluting it ten times with distilled water.

Macrocyclic Ketones:

No. 1: cyclopentadecanone (saturated compound)

No. 2: 3-methyl-cyclopentadecanone (saturated compound)

No. 3: cyclohexadecanone (saturated compound)

No. 4: 5-cyclohexadecen-1-one (unsaturated compound)

No. 5: 8-cyclohexadecen-1-one (unsaturated compound)

No. 6: cycloheptadecanone (saturated compound)

No. 7: 9-cycloheptadecen-1-one (unsaturated compound)

Used Strains:

Gram-positive rods (coryneform bacteria)
  Corynebacterium sp. (referred to as "C.sp")
  Propionibacterium acnes (referred to as "P.a")
  Brevibacterium epidermidis (referred to as "B.e")

Gram-positive coccus
  Staphylococcus epidermidis (referred to as "S.e")
  Staphylococcus aureus (referred to as "S.a")

Gram-negative rods
  Pseudomonas aeruginosa (referred to as "Ps.a")
  Escherichia coli (referred to as "E.c")

Used Culture Media:

For aerobic bacteria: normal bouillon medium (produced by Eiken Chemical Corporation)

For anaerobic bacteria: GAM bouillon "Nissui" (produced by Nissui Seiyaku Corporation)

Each culture medium of 100 ml was put in an Erlenmeyer flask having a capacity of 500 ml, suspension of each bacteria was inoculated to achieve $10^5$ CFU/ml, the test liquid was added into it so that the concentration of each macrocyclic ketone became 0 (blank), 10 and 100 ppm, respectively, and after a silicone gas-permeable plug was attached, at 37° C. for 10 hours, 80 rpm reciprocally shaking culture was conducted as to the aerobe and static culture was conducted as to the anaerobe, respectively. Thereafter, the turbidity of the culture liquid (absorbance at a wave length of 660 nm) was determined. In this examination, only propionibacterium acnes, which was strict anaerobe, was cultivated anaerobically.

As a result, as shown in Table 8, the macrocyclic ketones did not at all indicate a growth suppressing property against Gram-negative bacteria but indicate a growth suppressing property against Gram-positive bacteria. Among these, they indicated a particular growth suppressing property against coryneform bacteria, and particularly, in the macrocyclic ketones whose "n" is 1 or 2 in the aforementioned chemical formula (2), strong growth suppressing properties could be recognized against any strains of coryneform bacteria.

TABLE 8

| Macrocyclic ketone No. | Concentration ppm | Used strain | | | | | | |
| --- | --- | --- | --- | --- | --- | --- | --- | --- |
| | | Gram-positive | | | | | Gram-negative Rod | |
| | | Rod (coryneform bacteria) | | | Coccus | | | |
| | | C.sp | P.a | B.e | S.a | S.e | Ps.a | E.c |
| 1 | 0 | + | + | + | + | + | + | + |
| | 10 | − | − | + | + | + | + | + |
| | 100 | − | − | + | + | + | + | + |
| 2 | 0 | + | + | + | + | + | + | + |
| | 10 | − | − | + | + | + | + | + |
| | 100 | − | − | + | + | + | + | + |
| 3 | 0 | + | + | + | + | + | + | + |
| | 10 | − | − | − | + | + | + | + |
| | 100 | − | − | − | − | + | + | + |
| 4 | 0 | + | + | + | + | + | + | + |
| | 10 | − | − | − | + | + | + | + |
| | 100 | − | − | − | − | + | + | + |
| 5 | 0 | + | + | + | + | + | + | + |
| | 10 | − | − | − | + | + | + | + |
| | 100 | − | − | − | + | + | + | + |
| 6 | 0 | + | + | + | + | + | + | + |
| | 10 | − | − | − | + | + | + | + |
| | 100 | − | − | − | − | − | + | + |
| 7 | 0 | + | + | + | + | + | + | + |
| | 10 | − | − | − | + | + | + | + |
| | 100 | − | − | − | − | − | + | + |

− : growth; none
+ : growth; present

EXAMPLES

Examples 6 and Comparative Example 3
(deodorant lotion)

Each of 10 males having the armpit odor applied the deodorant lotions of Example 6 and Comparative Example 3 shown in Table 9 on the armpit after taking a bath, and the effect for suppressing the armpit odor after 10 hours was estimated. As a result, as shown in Table 10, in the deodorant lotion of Example 6, an effect for suppressing the armpit odor could be clearly recognized as compared with the deodorant lotion of Comparative Example 3. This Comparative Example 3 is the same as the aforementioned Comparative Example 2.

TABLE 9

| Component | Example 6 (wt. %) | Comparative Example 3 (wt. %) |
| --- | --- | --- |
| 5-cyclohexadecen-1-one | 0.1 | — |
| chlorohydroxyl aluminium | 10.0 | 10.0 |
| ethanol | 70.0 | 70.0 |
| polyoxyethylene oleylalcohol(20 E.O.) | 1.5 | 1.5 |
| aromatic | 0.1 | 0.1 |
| distilled water | remaining amount | remaining amount |

TABLE 10

| Estimation | Example 6 (Number of persons) | Comparative Example 3 (Number of persons) |
| --- | --- | --- |
| Very efficacious | 9 | 0 |
| Efficacious | 1 | 3 |
| A little efficacious | 0 | 6 |
| Not efficacious | 0 | 1 |
| Deteriorated | 0 | 0 |

Example 7 and Comparative Example 4 (cream for pimples)

Each of 10 males in twenties having pimples applied the cream of Example 7 shown in Table 11 onto the right half of the face and the cream of Comparative Example 4 onto the left half of the face after taking a bath, every day for one month. As a result, as shown in Table 12, in Example 7, an effect for treating pimples could be clearly recognized as compared with Comparative Example 4. Moreover, masking effect of sulfur smell was also recognized.

TABLE 11

| Component | Example 7 (wt. %) | Comparative Example 4 (wt. %) |
| --- | --- | --- |
| 9-cycloheptadecen-1-one | 0.3 | — |
| sulfur | 3.0 | 3.0 |
| glycerinemonostearate | 3.0 | 3.0 |
| polyoxyethylene oleylalcohol(20 E.O.) | 1.0 | 1.0 |
| beeswax | 3.0 | 3.0 |
| liquid paraffin | 10.0 | 10.0 |
| vaseline | 5.0 | 5.0 |
| squalene | 30.0 | 30.0 |
| propylene glycol | 5.0 | 5.0 |
| paraoxybutyl benzoate | 0.1 | 0.1 |
| aromatic | 0.05 | 0.05 |
| distilled water | remaining amount | remaining amount |

TABLE 12

| Estimation | Example 7 (Number of persons) | Comparative Example 4 (Number of persons) |
| --- | --- | --- |
| Very efficacious | 7 | 0 |
| Efficacious | 2 | 1 |
| A little efficacious | 1 | 2 |
| Not efficacious | 0 | 7 |
| Deteriorated | 0 | 0 |

Example 8 and Comparative Example 5 (antibacterial agent for clothes)

After taking a bath, each of 10 males put on the socks each sprayed with the antibacterial agent for clothes of Example 8 and the antibacterial agent for clothes of Comparative Example 5 shown in Table 13 for ten hours, and the intensity of the foot odor of the socks after wearing was estimated. As a result, as shown in Table 14, in Example 8, an effect for suppressing the foot odor could be clearly recognized as compared with Comparative Example 5.

TABLE 13

| Component | Example 8 (wt. %) | Comparative Example 5 (wt. %) |
| --- | --- | --- |
| 15-pentadecanolide | 1.0 | — |
| polyoxyethylene oleylalcohol(20 E.O.) | 1.0 | 1.0 |
| aromatic | 0.1 | 0.1 |
| ethanol | remaining amount | remaining amount |

TABLE 14

| Component | Example 8 (Number of persons) | Comparative Example 5 (Number of persons) |
| --- | --- | --- |
| Foot odor is not present at all. | 2 | 0 |
| Almost not present | 5 | 0 |
| slightly present | 3 | 3 |
| Foot odor is strong. | 0 | 5 |
| Very strong | 0 | 2 |

Industrial Applications of the Invention

The antibacterial agents containing the specified macrocyclic lactone or/and macrocyclic ketone indicate an excellent property for suppressing the growth against specified indigenous dermal bacteria, in particular, suppress the evolution of the body odor, and they are useful to cosmetics used for the purpose of preventing or treating pimples, and to clothes.

We claim:

1. An antibacterial agent selected from the group consisting of at least one of a macrocyclic lactone and a macrocyclic ketone, said macrocyclic lactone being represented by the following chemical formula 1, where "n" is an integer in the range of 0–2, the designations "---" are single bonds or any one portion of the portions shown by "---" is a double bond, and said macrocyclic ketone being represented by the following chemical formula (2), where "n" is an integer in the range of 0–2, R is a hydrogen atom or a methyl group, and the designations "---" are single bonds or any one portion of the portions shown by "---" is a double bond.

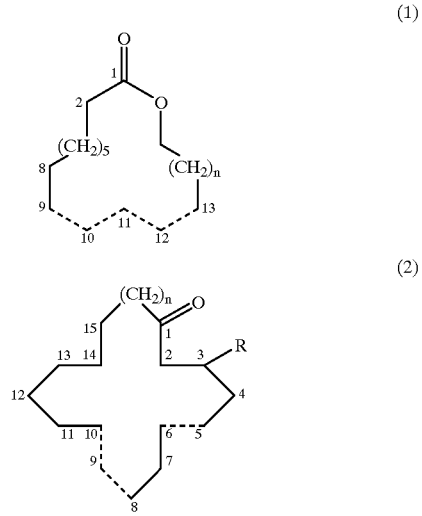

2. The antibacterial agent according to claim 1, wherein said macrocyclic lactone and macrocyclic ketone have a potency for suppressing the growth of indigenous dermal bacteria.

3. The antibacterial agent according to claim 2, wherein said indigenous dermal bacteria are coryneform bacteria.

4. The antibacterial agent according to claim 3, wherein said coryneform bacteria are at least one of bacteria of the genus Corynebacterium and the genus Propionibacterium.

5. The antibacterial agent according to claim 1, wherein said macrocyclic lactone is at least one selected from the group consisting of 14-tetradecanolide, 15-pentadecanolide, 11(or 12)-pentadecen-15-olide, 16-hexadecanolide and 9-hexadecen-16-olide.

6. The antibacterial agent according to claim 1, wherein said macrocyclic ketone is at least one selected from the group consisting of cyclopentadecanone, 3-methyl-cyclopentadecanone, cyclohexadecanone, 5-cyclohexadecen-1-one, 8-cyclohexadecen-1-one, cycloheptadecanone and 9-cycloheptadecen-1-one.

7. The antibacterial agent according to any one of claims 1 to 6, wherein said antibacterial agent has a property for suppressing the body odor or/and a property for suppressing pimples.

8. The antibacterial agent according to claim 7 combined with a cosmetic.

9. A cosmetic containing the antibacterial agent according to claim 7.

10. The cosmetic according to claim 9 having a property for suppressing body odor or/and a property for suppressing pimples.

11. A cloth impregnating the antibacterial agent according to claim 7.

12. The cloth according to claim 11 having at least an antibacterial/deodorizing effect.

* * * * *